United States Patent [19]
Funahashi et al.

[11] Patent Number: 4,718,992
[45] Date of Patent: Jan. 12, 1988

[54] TEST MEDIUM AND METHOD FOR DETECTING PHOSPHORUS SEGREGATES IN METALLIC MATERIAL

[75] Inventors: Yoshiko Funahashi; Yoshikazu Kamino; Yasuharu Matsumura; Senichi Harimaya, all of Chiba, Japan

[73] Assignees: Kawasaki Steel Corporation, Hyogo; Kawasaki Steel Techno-Research Corporation, Tokyo, both of Japan

[21] Appl. No.: 897,833

[22] Filed: Aug. 19, 1986

[30] Foreign Application Priority Data

Aug. 20, 1985 [JP] Japan .................................. 60-182765
Dec. 25, 1985 [JP] Japan .................................. 60-296120

[51] Int. Cl.⁴ .......................... C25F 3/06; G01N 33/20
[52] U.S. Cl. ....................................... 204/1 T; 204/140; 204/141.5; 436/78; 436/103
[58] Field of Search .................. 204/140, 141.5, 144, 204/144.5, 129.1, 129.2, 129.4, 129.75, 1 T; 422/56–58, 61; 436/103–105, 78

[56] References Cited

U.S. PATENT DOCUMENTS

| | | | |
|---|---|---|---|
| 3,425,805 | 4/1969 | Grobin | 436/103 |
| 3,530,045 | 9/1970 | Alburger | 204/1 T |
| 3,796,543 | 3/1974 | Kamphake | 436/103 |
| 4,643,978 | 2/1987 | Funahashi et al. | 436/78 |
| 4,643,979 | 2/1987 | Funahashi et al. | 436/78 |

FOREIGN PATENT DOCUMENTS 1130802  12/1984  U.S.S.R. ................................ 436/103

Primary Examiner—John F. Niebling
Assistant Examiner—Ben Hsing
Attorney, Agent, or Firm—Young & Thompson

[57] ABSTRACT

An aqueous electrolytic solution of a molybdate ion and an oxidizing agent is effective to detect phosphorus segregates in a metallic material, particularly cast steel through electrolysis. Segregated phosphorus can be detected by (a) applying a test sheet against a surface area of the metallic material to be examined for segregation, (b) introducing an aqueous electrolytic solution comprising 0.1 to 20% by weight of a molybdate ion and an oxidizing agent between the metallic material surface area and the sheet, (c) contacting a cathode plate with the sheet, (d) effecting electrolysis with the metallic material made anode, (e) removing the sheet from the metallic material surface, and (f) treating the sheet with a reducing agent.

15 Claims, 11 Drawing Figures

TEST MEDIUM AND METHOD FOR DETECTING PHOSPHORUS SEGREGATES IN METALLIC MATERIAL

BACKGROUND OF THE INVENTION

This invention relates to a test medium and method for detecting phosphorus segregates, and more particularly, to such a medium and method capable of rapidly and easily detecting the distribution of phosphorus in metallic materials such as continuously cast steel slabs and large-sized steel ingots by utilizing electrolysis.

It is well known in the art that continuously cast steel slabs and large-sized steel ingots have such elements as sulfur (S), phosphorus (P), manganese (Mn), silicon (Si), and carbon (C) locally concentrated or segregated in their central area, and these segregated elements have a great influence on the quality of steel products. In the prior art, such central segregation was judged by sulfur printing in iron-making works. This method is by attaching photographic paper impregnated with aqueous sulfuric acid to a polished cross section of a large-sized steel ingot, thereby detecting hydrogen sulfide given off from segregated sulfur as stains on the photographic paper. The distribution of sulfur is two-dimensionally developed on a photographic paper sheet.

As a new segregate detecting method substituting for the sulfur printing method, we developed a phosphorus printing method, that is, a method for detecting phosphorus segregates by selectively etching a phosphorus segregated area with a copper or silver nitrate solution, transferring phosphorus or iron to test paper, and subjecting the occluded phosphorus or iron to color development as disclosed in Japanese Patent Application Nos. 58-213497, 59-153799, 59-170227, 59-174828, and 59-180016.

One old method of detecting phosphorus is the phosphorus printing reported by M. Niessner in 1932. This method is by attaching filter paper which has been impregnated with liquid II shown below in Table 1 to a surface area of steel to be examined for 3 to 5 minutes, removing the paper from the steel surface, and thereafter dipping the filter paper in liquid I for 3 to 5 minutes, thereby producing a printed image.

TABLE 1

| Liquid I | |
| --- | --- |
| Saturated stannous chloride solution | 5 ml |
| Conc. hydrochloric acid | 50 ml |
| Water | 100 ml |
| Alum | minor amount |
| Liquid II | |
| Ammonium molybdate | 5 grams |
| Water | 100 ml |
| Nitric acid (specific gravity 1.2) | 35 ml |

Since specimen surface is maintained in contact with 1.8N nitric acid, the matrix is severely attacked and phosphorus is dissolved out there. When the removed test paper is dipped in liquid I, it turns blue over the entire surface. This method is only useful to estimate the amount of phosphorus in the matrix, but difficult to detect phosphorus segregates in commercial grade steels (see FIG. 6).

When it is desired to detect segregates in solidified stainless steel, the afore-mentioned sulfur and phosphorus printing methods are useless because any etching solutions used therein can attack or dissolve a surface area to be examined to an insufficient extent to detect segregates. There is a strong need for a phosphorus segregate detecting medium and method which are also applicable to stainless steel.

SUMMARY OF THE INVENTION

An object of the present invention is to provide a novel and improved test medium and method for detecting phosphorus segregates in a metallic material, particularly stainless steel as a printed image on a test sheet, which is equal in ease of operation and faster in detection of phosphorus segregates as compared with the conventional sulfur printing and phosphorus printing methods.

Another object of the present invention is to provide a method for detecting phosphorus segregates in a stainless steel having a relatively high chromium content.

A further object of the present invention is to provide a method for detecting phosphorus segregates in a stainless steel having a relatively low chromium content.

According to the present invention, there is provided a test medium for use in detecting phosphorus segregates in a metallic material through electrolysis.

In a first embodiment the test medium is in the form of an aqueous electrolytic solution containing 0.1 to 20% by weight of a molybdate ion and an effective amount of an oxidizing agent.

In a second embodiment, the test medium is in the form of a sheet impregnated with an aqueous electrolytic solution containing 0.1 to 20% by weight of a molybdate ion and an effective amount of an oxidizing agent.

In a third embodiment, the test medium is in the form of a sheet having an effective amount of a molybdate ion-producing substance incorporated therein in a dry state.

According to a first aspect of the present invention, there is provided a method for detecting phosphorus segregates in a metallic material, comprising the steps of:

(a) applying a test sheet against a surface area of the metallic material to be examined for segregation, (b) introducing an aqueous electrolytic solution comprising 0.1 to 20% by weight of a molybdate ion and an oxidizing agent between at least the metallic material surface area and the sheet, (c) contacting a cathode plate with the sheet, (d) effecting electrolysis with the metallic material made anode, (e) removing the sheet from the metallic material surface area, and (f) treating the sheet with a reagent comprising a reducing agent.

According to a second aspect of the present invention, there is provided a method for detecting phosphorus segregates in a metallic material, comprising the steps of:

maintaining a solution of an oxidizing agent in contact with a surface area of the metallic material to be examined for segregation for a sufficient time, removing the oxidizing solution from the surface area, applying a test sheet against the metallic material surface area, introducing an aqueous electrolytic solution comprising 0.1 to 20% by weight of a molybdate ion and an oxidizing agent between at least the metallic material surface area and the sheet, contacting a cathode plate with the sheet, effecting electrolysis with said metallic material made anode, removing the sheet from the metallic material surface area, and treating the sheet with a reagent comprising a reducing agent.

DETAILED DESCRIPTION OF THE INVENTION

In continuously cast slabs and large-sized ingots of stainless steel having a relatively high chromium content, phosphorus has a relatively high rate of segregation upon solidification like sulfur and tends to substantially concentrate at the last-to-solidify site. Phosphorus rich portions are lower in natural electrode potential and preferentially dissolved in etching solution.

Paying attention to the fact that it is very important in evaluating internal defects in steel to detect phosphorus segregated sites, we have made extensive investigations on the detection of phosphorus segregates in steel stocks. We have discovered that phosphorus segregated sites on a steel surface can be clearly detected with a high resolving power by interposing an electrolytic solution containing 0.1 to 20% by weight of molybdate ion and an oxidizing agent between a surface area of steel to be examined and a test sheet, subjecting the surface area to anodic polarization with the aid of the electrolytic solution to electrolytically dissolve phosphorus in the surface area, and treating the test sheet having phosphorus occluded therein with a reagent comprising a reducing agent, whereby a phosphorus segregation pattern is to be printed on the sheet.

Following is the detail of our discovery about the detection of phosphorus segregates in a metallic material, particularly stainless steel. It is well known that stainless steel is corrosion resistant because it has a dense oxide coating on the surface. To dissolve stainless steel, it is necessary first to dissolve away the surface oxide coating. Conventional chemical etching would not only take a very long time to dissolve the oxide coating, prolonging the overall time required in phosphorus detection, but is also difficult to dissolve the matrix iron (over a surface area to be examined) to a necessary extent to detect phosphorus.

As a pre-etching step useful in phosphorus printing, we have intended to forcedly dissolve stainless steel by anodic electrolysis. We have found that a surface area of steel to be examined for phosphorus segregation can be rapidly and readily dissolved and phosphorus segregates can be detected as a clear image by applying a test sheet impregnated with an appropriate electrolytic solution against the steel surface area, subjecting the specimen to anodic polarization to effect electrolysis in a trans-passive region, thereby causing phosphorus to penetrate into the test sheet, and treating the phosphorus in the sheet with a coloring reagent for color development.

Figure 1:
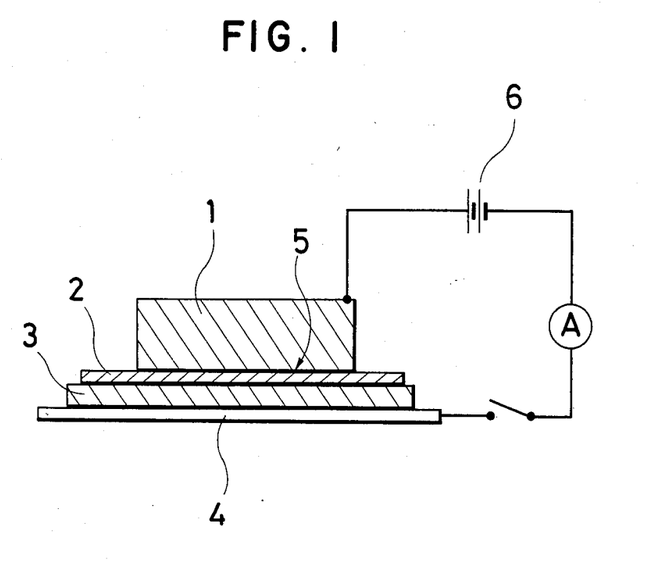
FIG. 1 is a schematic view illustrating an arrangement for electrolytic etching of a steel specimen according to the present invention.

Referring to FIG. 1, there is illustrated an arrangement for electrolytic etching of a steel specimen, which is used as a pre-etching according to the present method. A specimen 1 having a surface area 5 to be examined for phosphorus segregation is placed on a test sheet 3 which rests on a cathode plate 4. An electrolytic solution 2 containing 0.1 to 20% by weight of molybdate ion and an oxidizing agent is introduced between the specimen 1 and the test sheet 3. That is, the surface area 5 is held in contact with the electrolytic solution 2. The specimen 1 and the cathode plate 4 are connected to the anode and cathode terminals of a electrical power source 6, respectively. When a switch is closed to conduct current, the surface area 5 is subject to anodic polarization and the cathode plate 4 to cathodic polarization. The figure is illustrated for convenience of understanding although the test sheet 3 is preferably impregnated with the electrolytic solution 2.

With this arrangement having the electrolytic solution 2 sandwiched between the specimen 1 and the cathode plate 4, voltage is applied across the sandwich structure, preferably by an electrolysis-at-constant-current process at a current density of 1 to 10 mA/cm$^2$ (milliamperes per square centimeter) for about 2 to 20 minutes, thereby dissolving the specimen surface area 5 in a predetermined amount. Phosphorus is then dissolved in the electrolytic solution and transferred to the test sheet 3 in contact therewith.

Since the electrolytic step is employed as a pre-etching step according to the present method, the surface area to be examined can be dissolved in any controlled quantity by changing electrolytic conditions. Thus even a sample having a low content of phosphorus can be positively detected for phosphorus segregation.

The specimen used herein may include a surface area of a shape of metallic material to be examined for segregation including continuously cast slabs and large-sized steel ingots, especially stainless steel as well as a usual specimen sectioned from such a shape. In either case, the surface area to be examined must be properly cleaned prior to testing.

The cathode plate used herein may be formed from any electrically conductive materials including aluminum, platinum, copper, stainless steel, and graphite.

The test sheets used herein may be sheets of such materials as wood and synthetic resins as well as sheets of paper insofar as they can bear electrolytic solution. The preferred test sheet is a wood-free paper sheet having a powdery inorganic compound filled on one surface and gelatin solution coated thereon. For example, a sheet of wood-free paper made of hydrophilic pulp fibers is coated on one surface with an inorganic compound powder such as barium sulfate, titanium white, talc, and clay, to fill voids in the fiber layer to provide a smoothened surface. The inorganic filler is also useful in improving the opacity of the paper surface and the contrast of a color developing layer.

In order to obtain a clear printed image, it is important to hold the test sheet 3 in close contact with the specimen surface area 5 to be examined through the electrolytic solution 2 while preventing diffusion of the electrolytic solution. The test sheet can be made more adherent by fixing a tacky water-soluble high molecular weight agent such as gelatin, polyvinyl alcohol, and starch to the sheet surface. The adherent test sheet is effective in preventing a printed image from being blurred due to diffusion of the electrolytic solution.

It is preferred to interpose a water-absorbing insert such as filter paper between the test sheet and the cathode plate, the insert being fully impregnated with the electrolytic solution. The test sheet is then replenished with the electrolytic solution from the insert. Although electrolysis can be effected with only the test sheet, the use of such an additional impregnated insert increases the electrolytic quantity available on the test surface area. In addition to filter paper, any desired water-absorbing member, for example, fibrous materials such as absorbent wadding and fabric, gel-like materials, and leather may also be used as the insert.

The electrolytic solution with which the test sheet is impregnated may be a solution containing a phosphorus coloring agent and an oxidizing agent, desirably 0.1% to 20% by weight of molybdate ion in 0.5N to 7N nitric acid.

The oxidizing agent is used mainly for two reasons. Since phosphorus is dissolved out of the phosphorus segregated site in the form of phosphoric acid, the phosphoric acid must be oxidized to ortho-phosphoric acid before it is reacted with the coloring agent, molybdate ion.

The second reason is that if iron dissolved out of steel or stainless steel is present as $Fe^{2+}$, then the molybdate salt is reduced therewith to develop its color (blue color), failing to detect phosphorus segregates. Thus the iron dissolved from the matrix must take the form of $Fe^{3+}$. Since stainless steel is immediately passivated in an oxidizing solution, the dissolution state during anodic polarization is limited to trans-passive dissolution state and iron is naturally dissolved as $Fe^{3+}$.

A molybdate salt such as ammonium molybdate is added to the electrolytic solution for the purpose of immediately precipitating the dissolved phosphorus as phosphorus molybdate (molybdenum yellow) to suppress diffusion of phosphate residue occluded in the test sheet, thereby preventing a blur of a printed image. Some illustrative, non-limiting examples of the molybdate salts used herein include ammonium molybdate, sodium molybdate, lithium molybdate, magnesium molybdate, calcium molybdate, and potassium molybdate.

The concentration of nitric acid added to the electrolytic solution is limited to the range of 0.5N to 7N and that of molybdate ion limited to the range of 0.1% to 20% by weight. Formation of molybdenum yellow is insufficient if the acid concentration is outside the above-defined range or the molybdate ion concentration is less than 0.1% by weight. Molybdic acid itself develops its color to render it impossible to distinguish phosphorus segregates if present in excess of 20% by weight.

Other oxidizing solutions such as sulfuric acid-chromic acid and sulfuric acid-hydrogen peroxide solutions may be used instead of nitric acid insofar as they do not disturb color development of phosphorus.

The phosphorus segregate detecting medium according to the present invention may be used in any desired combinations of sheet and solution as illustrated below.

A first embodiment is to use an aqueous solution containing an oxidizing agent, especially 0.5 to 7N nitric acid and 0.1 to 20% by weight of molybdate ion in combination with a dry free sheet. This embodiment may be practiced by first attaching a dry free sheet to a specimen surface area to be examined, introducing the solution between the sheet and the surface area by spraying, coating, or similar techniques, and then conducting electric current. The solution may be an aqueous solution or an alcoholic solution.

A second embodiment is to use the solution as a wet sheet impregnated with the same. This embodiment may be practiced by attaching a wet loaded sheet to the specimen surface area and conducting electric current.

A third embodiment is to use a dry loaded sheet which is prepared by impregnating a dry free sheet with a molybdate ion-containing solution followed by drying. That is, the dry loaded sheet is a sheet having the requisite agent loaded therein in dry state. This embodiment may be practiced by attaching the dry loaded sheet to the specimen surface area, introducing a solution of an oxidizing agent, especially 0.5 to 7N nitric acid between the sheet and the surface area so as to bring the molybdate concentration in the above-defined range, and conducting electric current.

By effecting electrolysis in a solution of oxidizing agent and molybdate ion between a surface area of steel to be examined and a test sheet as described above, phosphorus is dissolved out of the surface area and occluded in the test sheet as molybdenum yellow. By immersing the test sheet in a solution of a reducing agent, the phosphorus is converted into molybdenum blue which develops a blue color. With this color development, phosphorus segregates can be detected.

Examples of the reducing agents used herein include stannous chloride, hydroquinone, hydrazine sulfate, and ascorbic acid. When stannous chloride is used, solutions containing 0.1 to 20% by weight of stannous chloride and 0.5 to 6N of hydrochloric acid are preferred. Less than 0.1% by weight of stannous chloride provides a less reducing power whereas the reducing power is no longer increased in excess of 20% by weight. Less than 0.5N of hydrochloric acid undesirably allows molybdic acid itself to be reduced whereas concentrated hydrochloric acid higher than 6N gives off hydrochloric acid vapor, adversely affecting the working environment. The other reducing agents may be used so as to provide an equivalent reducing power.

The method according to the first aspect of the present invention has been described. If iron is dissolved out in $Fe^{2+}$ form (active dissolution) during electric conduction, the phosphorus coloring agent is reduced therewith to develop a blue color all over the test sheet, failing in phosphorus segregate detection. To avoid such an unfavorable phenomenon, iron must be dissolved in $Fe^{3+}$ form (over-passive dissolution) as previously described. This means that the method of the first aspect is not applicable to those types of steel which cannot be dissolved in a trans-passive region. More particularly, when stainless steels are subjected to electrolysis in an oxidizing solution, those types of steel having a relatively high chromium content can be dissolved in the trans-passive region. But, the method of the first aspect is not applicable to those types of steel having a relatively low chromium content because dissolution takes place in an active region.

We have discovered that the method of the first aspect can be applied to those types of steel having a relatively low chromium content if the method is modified by adding the step of maintaining a solution of an oxidizing agent in contact with a surface area to be examined for a sufficient time prior to applying a test sheet against the surface area.

The passive coating formed on the surface of stainless steel will be described in more detail.

When a steel having a high Cr content (generally 16% or higher) is dipped in an electrolytic solution containing an oxidizing agent, a passive coating is immediately formed as a surface layer of the steel. This coating is dense and stable, and thus resistant to breakage. Anodic polarization causes the coating to progressively change into a trans-passive coating. That is, dissolution takes place in the trans-passive region.

On the other hand, a steel having a low Cr content (usually less than 16%, for example, 13Cr steel) forms an unstable passive coating. Thus, formation and dissolution of a coating are repeated. Electric conduction causes iron to be dissolved out as $Fe^{2+}$, with which the coloring agent of molybdate salt is reduced to develop a blue color over the sheet.

It is thought that the active dissolution inherent to a low Cr content steel can be suppressed by previously forming a stable coating thereon. We have thus found that a stable passive coating can be formed on a surface area of such a steel to be examined by contacting a solution containing a strong oxidizing agent with the surface area, and trans-passive dissolution then takes place during electric conduction.

The oxidizing agent-containing solutions used herein are solutions of nitric acid, chromic acid, and hydrogen peroxide and solutions containing metal ions such as $Ce^{4+}$ and $Fe^{3+}$. Any oxidizing solutions may be used insofar as they do not disturb subsequent color development of phosphorus. When nitric acid is used, its concentration may be at least 0.5N. When $Ce^{4+}$ is used, its concentration may be at least 0.01 mol/liter. A stable oxide coating is not formed below these concentration limits. Other oxidizing agents may be used in amounts to provide an equivalent oxidizing power.

The oxidizing solution serving as the oxide layer-forming agent may be used in various ways.

In a first embodiment, a water-absorbing sheet is prepared. It is impregnated with the oxidizing solution. The wet sheet is attached to a surface area to be examined. The wet sheet is allowed to stand in contact with the surface area for a sufficient time to form a stable passive oxide layer.

A second embodiment uses a dry sheet and the oxidizing solution. The sheet is attached to the surface area to be examined, and the oxidizing solution is applied to the sheet so that the solution be present between the sheet and the surface area.

A third embodiment uses a dry loaded sheet which is prepared by impregnating a dry free sheet with an oxidizing agent-containing solution followed by drying. That is, the dry loaded sheet is a sheet having the oxidizing agent loaded therein in dry state. This embodiment may be practiced by attaching the dry loaded sheet to the specimen surface area, and applying water or an oxidizing solution to the sheet so that the solution of oxidizing agent be present between the sheet and the surface area.

It is also possible to directly contact the oxidizing solution to the surface area by coating or the like without using a sheet.

The sheets used in these embodiments may be any desired sheet-like articles of materials capable of bearing the oxidizing solution such as wood, fabric, synthetic resins, and leather. Filter paper is usually used.

A stable passive coating is formed on a surface area to be examined by contacting an oxidizing solution therewith as described above. After formation of a stable passive coating, the method according to the second aspect follows the steps of the method according to the first aspect. The method according to the second aspect may be applicable to high Cr content steels as well as low Cr content steels.

EXAMPLES

Examples of the present invention are presented below by way of illustration and not by way of limitation.

EXAMPLE 1

Figure 2:
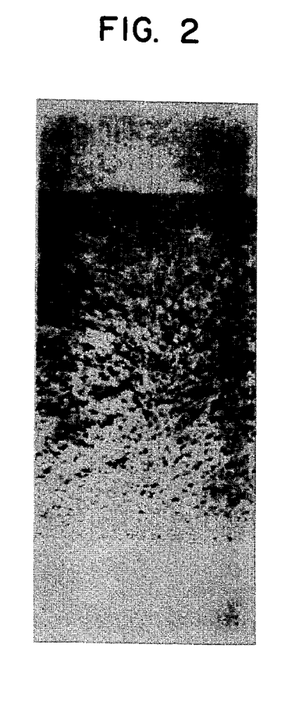
FIGS. 2, 3, and 4 are photographs of a phosphorus segregate image obtained in Examples 1, 2, and 3, respectively.

A steel specimen was sectioned from a segregated region of a continuously cast slab of SUS 304 stainless steel having a phosphorus content of 0.02% by weight. It was polished with #150 emery paper and fully cleaned with absorbent wadding. A wet test paper sheet which was impregnated with an aqueous solution of 2% by weight ammonium molybdate and 1.75N nitric acid was applied against a surface area of the specimen to be examined for segregation. An electrical connection was set by placing a cathode plate in contact with the test sheet and connecting the specimen to serve as an anode. Electrolysis at constant current was conducted for 10 minutes at a current density of 2 mA/cm$^2$. The test paper was peeled from the specimen surface area, immersed in an aqueous solution of 7% by weight of stannous chloride and 4N hydrochloric acid for 5 minutes, and then fully rinsed with water. There was obtained a printed image as shown in FIG. 2.

EXAMPLE 2

Figure 3:
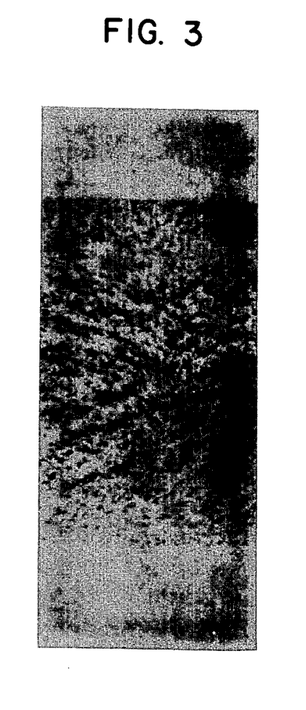

A steel specimen was sectioned from a segregated region of a continuously cast slab of SUS 304 stainless steel having a phosphorus content of 0.02% by weight. It was polished with #150 emery paper and fully cleaned with absorbent wadding. A test paper sheet was applied against a surface area of the specimen to be examined for segregation. The sheet was wetted with an aqueous solution of 3% by weight ammonium molybdate and 3.5N nitric acid. A cathode plate was placed in contact with the test sheet with the specimen made anode. Electrolysis at constant current was conducted for 5 minutes at a current density of 5 mA/cm$^2$. The test paper was peeled from the specimen surface area, immersed in an aqueous solution of 7% by weight of stannous chloride and 4N hydrochloric acid for 5 minutes, and then fully rinsed with water. There was obtained a printed image as shown in FIG. 3.

EXAMPLE 3

Figure 4:
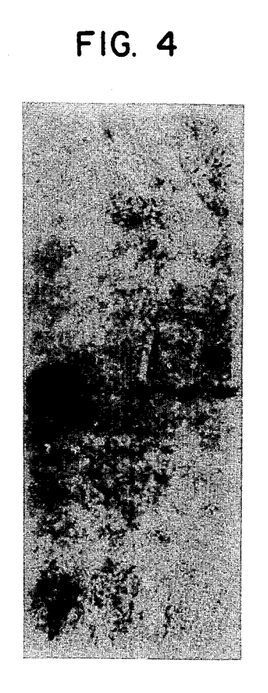

A steel specimen was sectioned from a segregated region of a continuously cast slab of SUS 430 stainless steel having a phosphorus content of 0.02% by weight. It was polished with #150 emery paper and fully cleaned with absorbent wadding. A dry test paper sheet having ammonium molybdate contained in an amount of 1.2 grams per square meter was applied against a surface area of the specimen to be examined for segregation. The sheet was evenly wetted with 4N nitric acid solution by wiping with absorbent wadding impregnated therewith. A cathode plate was placed in contact with the test sheet with the specimen made anode. Electrolysis at constant current was conducted for 6 minutes at a current density of 4 mA/cm$^2$. The test paper was removed from the specimen surface area, immersed in an aqueous solution of 7% by weight of stannous chloride and 4N hydrochloric acid for 5 minutes, and then fully rinsed with water. There was obtained a printed image as shown in FIG. 4.

COMPARATIVE EXAMPLE 1

Figure 5:
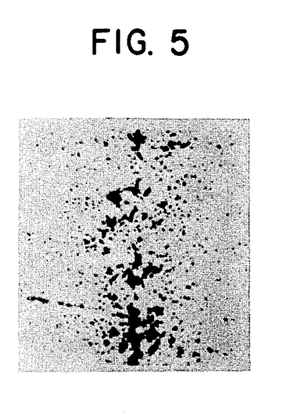
FIGS. 5 and 6 are photographs of a phosphorus segregate image obtained in Comparative Examples 1 and 2 according to prior art phosphorus printing methods, respectively.

A steel specimen was sectioned from a segregated region of a continuously cast slab of ordinary carbon steel having a phosphorus content of 0.02% by weight. It was polished with #180 emery paper and fully cleaned with absorbent wadding wetted with ethanol. It was immersed for 5 minutes in a 5% by volume hydrochloric acid in ethanol solution for etching, and then fully washed with alcohol. A wet test paper coupon which was impregnated with an aqueous solution of 5% by weight of silver nitrate (AgNO$_3$) was attached to a surface area of the specimen to be examined for segregation and maintained in pressure contact for 2 minutes. The test paper having an image of segregates developed was removed from the specimen surface and fixed with an aqueous solution of 10% by weight of sodium thiosulfate. There was obtained a printed image as shown in FIG. 5.

COMPARATIVE EXAMPLE 2

Figure 6:
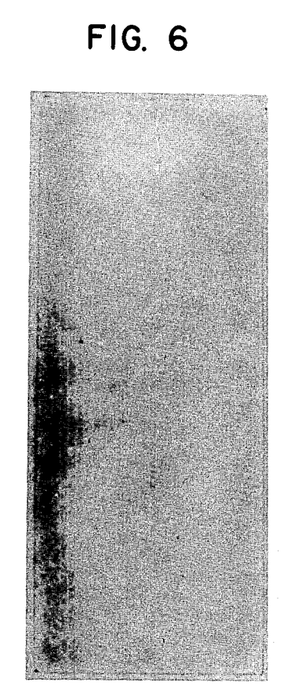

A specimen was prepared by the same procedure as in Example 3. A filter paper impregnated with liquid A having the following composition was held for 5 minutes in close contact with a surface area of the specimen to be examined. The filter paper was peeled from the specimen surface, then immersed for 7 minutes in liquid B having the following composition, and fully rinsed with water. There was obtained a printed image as shown in FIG. 6.

Liquid A
 Ammonium molybdate: 5 grams
 Water: 100 ml
 Nitric acid (specific gravity 1.2): 35 ml
Liquid B
 Saturated stannous chloride solution: 5 ml
 Conc. hydrochloric acid: 50 ml
 Water: 100 ml
 Alum: minor amount It is seen that the printed images (FIGS. 2-4) obtained by the present method are remarkably improved in resolving power to such an extent that a microscopic structure is clearly detected as well as central segregates, as compared with the printed images (FIGS. 5-6) by the prior art methods. The present method is thus effective particularly in the detection of phosphorus segregates in stainless steel which is difficult with the prior art methods.

EXAMPLE 4

Figure 7:
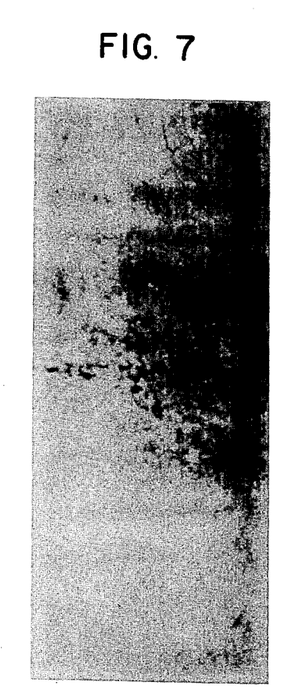
FIGS. 7, 8, 9, and 10 are photographs of a phosphorus segregate image obtained in Examples 4, 5, 6, and 7, respectively.

The subject to be examined was a continuously cast slab of SUS 410 stainless steel having a chromium content of 13% by weight and a phosphorus content of 0.028% by weight. A cross section of a segregated region of the steel was polished with #150 emery paper and fully cleaned with absorbent wadding. A wet paper sheet which was impregnated with an aqueous solution of 4.5N nitric acid was applied against a surface area to be examined for segregation. After a 10 minutes contact of nitric acid for oxidation, the sheet was removed from the surface area. Thereafter, a wet test paper sheet which was impregnated with an aqueous solution of 6% by weight ammonium molybdate and 4.5N nitric acid was applied against the surface area. An electrical connection was set by placing a cathode plate in contact with the test sheet and connecting the steel to serve as an anode. Electrolysis at constant current was conducted for 10 minutes at a current density of 3 mA/cm$^2$. The test sheet was peeled from the surface area, immersed in an aqueous solution of 7% by weight of stannous chloride and 4N hydrochloric acid for 5 minutes, and then fully rinsed with water. There was obtained a printed image as shown in FIG. 7.

EXAMPLE 5

Figure 8:
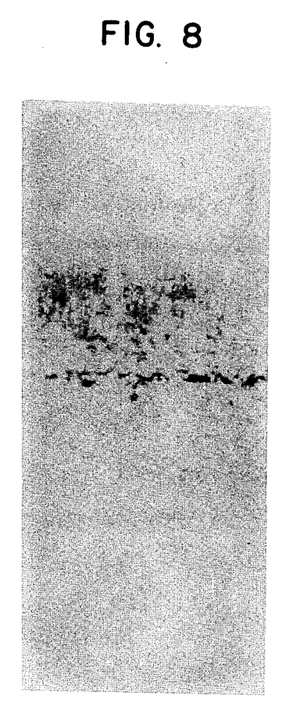

The subject to be examined was the same SUS 410 stainless steel as in Example 4. A cross section of a segregated region of the steel was polished with #150 emery paper and fully cleaned with absorbent wadding. A paper sheet was applied against a surface area to be examined for segregation. The sheet was wetted with an aqueous solution of 1% by weight potassium dichromate and 2N nitric acid. After an about 15 minutes contact with the solution, the sheet was removed from the surface area. Thereafter, a dry test paper sheet which contained 1.2 grams/m$^2$ of ammonium molybdate and 0.4 grams/m$^2$ of ammonium cerium nitrate was applied against the surface area. The test sheet was evenly wetted with 4N nitric acid solution by wiping with absorbent wadding impregnated therewith. A cathode plate was placed in contact with the test sheet with the steel made anode. Electrolysis at constant current was conducted for 5 minutes at a current density of 5 mA/cm$^2$. The test sheet was peeled from the surface area, immersed in an aqueous solution of 7% by weight of stannous chloride and 4N hydrochloric acid for 5 minutes, and then fully rinsed with water. There was obtained a printed image as shown in FIG. 8.

EXAMPLE 6

Figure 9:
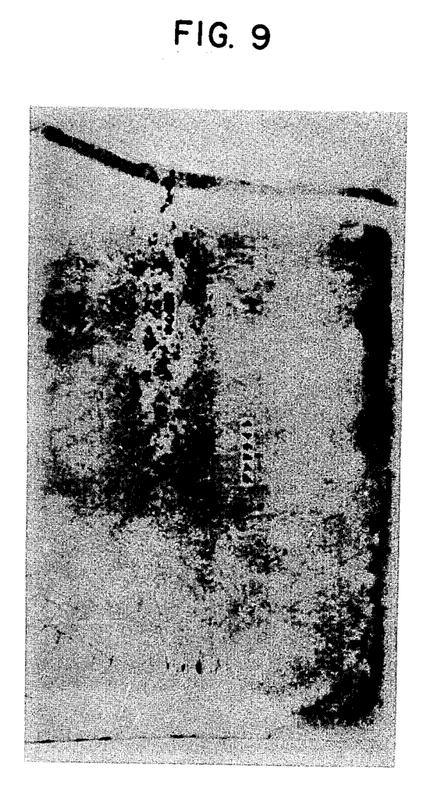

The subject to be examined was a continuously cast slab of SUS 420 stainless steel having a chromium content of 13% by weight and a phosphorus content of 0.03% by weight. A cross section of a segregated region of the steel was polished with #150 emery paper and fully cleaned with absorbent wadding. A dry paper sheet containing 0.5 grams/m$^2$ of ammonium cerium nitrate was applied against a surface area to be examined for segregation. The sheet was evenly wetted with 4N sulfuric acid by wiping with absorbent wadding impregnated therewith. After allowing to stand for about 20 minutes, the sheet was removed from the surface area. Thereafter, a test paper sheet was applied against the surface area. The sheet was evenly wetted by wiping with absorbent wadding impregnated with an aqueous solution of 6% by weight ammonium molybdate and 3N nitric acid. A cathode plate was placed in contact with the test sheet with the steel made anode. Electrolysis at constant current was conducted for 15 minutes at a current density of 3 mA/cm$^2$. The test sheet was peeled from the surface area, immersed in an aqueous solution of 7% by weight of stannous chloride and 4N hydrochloric acid for 5 minutes, and then fully rinsed with water. There was obtained a printed image as shown in FIG. 9.

EXAMPLE 7

Figure 10:
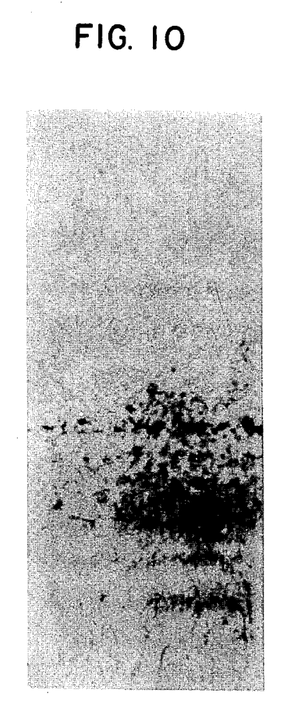

The subject to be examined was the same SUS 410 stainless steel as in Example 4. A cross section of a segregated region of the steel was polished with #150 emery paper and fully cleaned with absorbent wadding. The specimen was immersed for 15 minutes in 6N nitric acid solution. The specimen was removed from the nitric acid solution and fully washed with water. A wet test paper sheet which was impregnated with an aqueous solution of 6% by weight ammonium molybdate and 4.5N nitric acid was applied against a surface area of the specimen to be examined for segregation. A cathode plate was placed in contact with the test sheet with the steel made anode. Electrolysis at constant current was conducted for 10 minutes at a current density of 4 mA/cm$^2$. The test sheet was peeled from the surface area, immersed in an aqueous solution of 7% by weight of stannous chloride and 4N hydrochloric acid for 10 minutes, and then fully rinsed with water. There was obtained a printed image as shown in FIG. 10.

COMPARATIVE EXAMPLE 3

Figure 11:
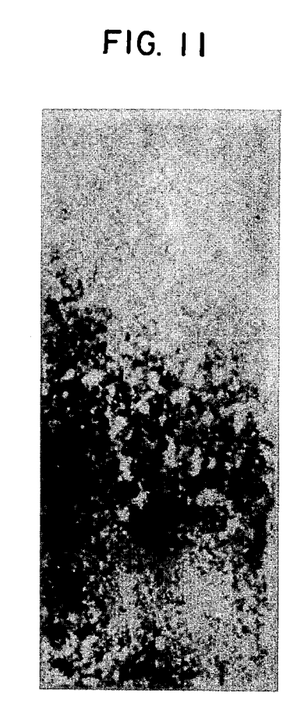
FIG. 11 is a photograph of a phosphorus segregate image obtained in Comparative Example 3 according to prior art phosphorus printing method.

A cross section of a segregated region of a continuously cast slab of SUS 410 stainless steel was polished with #400 emery paper and fully cleaned with absorbent wadding. A dry test paper sheet containing 1.2 grams/m$^2$ of ammonium molybdate was applied against a surface area to be examined for segregation. The test sheet was evenly wetted with 3N nitric acid by wiping with absorbent wadding impregnated therewith. A cathode plate was placed in contact with the test sheet with the steel made anode. Electrolysis at constant current was conducted for 10 minutes at a current density of 5 mA/cm$^2$. The test sheet was peeled from the surface area, immersed in an aqueous solution of 7% by weight of stannous chloride and 4N hydrochloric acid for 5 minutes, and then fully rinsed with water. There was obtained a printed image as shown in FIG. 11.

The electrolytic phosphorus segregation detecting method of the present invention which employs electrolysis for pre-etching allows a subject surface area to be dissolved in any desired amount and can thus detect phosphorus segregates even in samples having a very low content of phosphorus.

Since the electrolytic step per se is very easy to carry out, the present method is a convenient central segregation detecting method readily applicable to large-sized steel ingots and continuously cast slabs in casting works. The present method is useful particularly in the detection of phosphorus segregates in stainless steel which is difficult with the prior art methods. Even in the case of low Cr content stainless steel, phosphorus segregates can be effectively detected by forming an trans-passivated film by a pretreatment prior to electrolysis.

The phosphorus segregate detecting medium of the present invention may be used in any desired form as an electrolytic solution, a wet sheet impregnated with an electrolytic solution, and a dry sheet impregnated with an electrolytic solution followed by drying. In detecting phosphorus segregates, the present medium has additional benefits of ease and efficiency of operation and convenience of application in commercial works. A further benefit is that printed sheets may be recorded and stored.

What is claimed:

1. A method for detecting phosphorus segregates in a metallic material, comprising the steps of:
   (a) applying a test sheet against a surface area of the metallic material to be examined for segregation,
   (b) introducing an aqueous electrolytic solution comprising 0.1 to 20% by weight of a molybdate ion and an oxidizing agent between at least the metallic material surface area and the sheet,
   (c) contacting a cathode plate with said sheet,
   (d) effecting electrolysis with said metallic material made anode,
   (e) removing the sheet from the metallic material surface area, and
   (f) treating the sheet with a reagent comprising a reducing agent.

2. A method according to claim 1 wherein the electrolysis is carried out by an electrolysis-at-constant-current process at a current density of 1 to 10 mA/cm$^2$ for about 2 to 20 minutes.

3. A method according to claim 1 wherein the electrolytic solution contains 0.5 to 7N nitric acid as the oxidizing agent.

4. A method according to claim 1 wherein the electrolytic solution contains at least one member selected from the group consisting of ammonium molybdate, sodium molybdate, lithium molybdate, magnesium molybdate, calcium molybdate, and potassium molybdate.

5. A method according to claim 1 wherein the reducing agent is selected from the group consisting of stannous chloride, hydroquinone, hydrazine sulfate, and ascorbic acid.

6. A method according to claim 5 wherein the reagent comprising a reducing agent is a solution containing 0.1 to 20% by weight of stannous chloride and 0.5 to 6N of hydrochloric acid.

7. A method according to claim 1 wherein the test sheet is impregnated with an aqueous solution containing 0.1 to 20% by weight of a molybdate ion and an oxidizing agent to combine steps (a) and (b).

8. A method for detecting phosphorus segregates in a metallic material, comprising the steps of:
   (a) maintaining a solution of an oxidizing agent in contact with a surface area of the metallic material to be examined for segregation for a time sufficient to produce on said surface area a stable passive oxide layer,
   (b) applying a test sheet against the metallic material surface area,
   (c) introducing an aqueous electrolytic solution comprising 0.1 to 20% by weight of a molybdate ion and an oxidizing agent between at least the metallic material surface area and the sheet,
   (d) contacting a cathode plate with said sheet,
   (e) effecting electrolysis with said metallic material made anode,
   (f) removing the sheet from the metallic material surface area, and
   (g) treating the sheet with a reagent comprising a reducing agent.

9. A method according to claim 8 wherein the oxidizing solution is selected from the group consisting of solutions of nitric acid, chromic acid, and hydrogen peroxide, and solution containing $Ce^{4+}$ and $Fe^{3+}$.

10. A method according to claim 8 wherein the electrolysis is carried out by an electrolysis-at-constant-current process at a current density of 1 to 10 mA/cm$^2$ for about 2 to 20 minutes.

11. A method according to claim 8 wherein the electrolytic solution contains 0.5 to 7N nitric acid as the oxidizing agent.

12. A method according to claim 8 wherein the electrolytic solution contains at least one member selected from the group consisting of ammonium molybdate, sodium molybdate, lithium molybdate, magnesium molybdate, calcium molybdate, and potassium molybdate.

13. A method according to claim 8 wherein the reducing agent is selected from the group consisting of stannous chloride, hydroquinone, hydrazine sulfate, and ascorbic acid.

14. A method according to claim 13 wherein the reagent comprising a reducing agent is a solution containing 0.1 to 20% by weight of stannous chloride and 0.5 to 6N of hydrochloric acid.

15. A method according to claim 8 wherein the test sheet is impregnated with an aqueous solution containing 0.1 to 20% by weight of a molybdate ion and an oxidizing agent to combine steps (b) and (c).

* * * * *